US005986063A

United States Patent [19]

Etzel

[11] Patent Number: 5,986,063

[45] Date of Patent: Nov. 16, 1999

[54] ISOLATING β-LACTOGLOBULIN AND α-LACTALBUMIN BY ELUTING FROM A CATION EXCHANGER WITHOUT SODIUM CHLORIDE

[75] Inventor: Mark R. Etzel, Madison, Wis.

[73] Assignee: Wisconsin Alumni Research Foundation, Madison, Wis.

[21] Appl. No.: 09/126,904

[22] Filed: Jul. 31, 1998

[51] Int. Cl.[6] .......................... C07K 1/18; C07K 14/435; A23J 1/20

[52] U.S. Cl. .......................... 530/366; 426/580; 426/583; 426/657; 530/394; 530/416

[58] Field of Search .................................... 530/416, 365, 530/366, 394; 426/580, 583, 657

[56] References Cited

U.S. PATENT DOCUMENTS 5,516,675 5/1996 Uchida et al. .......................... 435/192

*Primary Examiner*—David M. Naff

*Attorney, Agent, or Firm*—DeWitt Ross & Stevens S.C.

[57] ABSTRACT

A method is provided for isolating the proteins, β-lactoglobulin and α-lactalbumin, from whey with a single cation exchanger, and using different pH values for eluting the proteins as separate fractions without using salt elution. A whey protein solution is adjusted to a pH of less than about 4.5. The solution is contacted with a cation exchanger to obtain a bound fraction containing α-lactalbumin and β-lactoglobulin. The bound fraction is adjusted to a pH of about 4.0 to 6.0 and a β-lactoglobulin fraction is eluted at this pH in the absence of sodium chloride. The pH of an remaining bound fraction is adjusted to about 6.5 or greater and an α-lactalbumin fraction is eluted. The method is advantageously conducted at elevated temperatures ranging from 35° C. to 50° C. The ion exchanger may be cross-linked polymeric beads made of cellulose, agarose or dextran, or a microporous polymeric membrane made of regenerated cellulose, polysulfone or cellulose acetate, and may contain charged immobilized molecules such as carboxymethyl or sulfopropyl moieties.

6 Claims, 9 Drawing Sheets

ISOLATING β-LACTOGLOBULIN AND α-LACTALBUMIN BY ELUTING FROM A CATION EXCHANGER WITHOUT SODIUM CHLORIDE

U.S. GOVERNMENT SUPPORT

This invention was made with United States government support awarded by the following agency: NSF Grant No. BES-9631962. The United States has certain rights in this invention.

BIBLIOGRAPHY

Complete bibliographic citations of the references referred to herein can be found in the Bibliography section, immediately preceding the claims.

FIELD OF THE INVENTION

This invention is directed to a process of selectively fractionating α-lactalbumin and β-lactoglobulin from whey using cation exchange. Specifically, the present invention is directed to a single cation-exchange method that produces both proteins in a substantially purified state.

DESCRIPTION OF THE PRIOR ART

Two significant proteins in whey are alpha-lactalbumin (α-lactalbumin) and beta-lactoglobulin (β-lactoglobulin). β-Lactoglobulin is a characteristic protein in milk of ruminants, but does not occur in human milk. α-Lactalbumin is found in the milk of all mammals and represents a major protein in human milk. This protein is largely used both in preparation of humanized milk and compositions of non-allergenic milk products for infants who are allergic to β-lactoglobulin in cow's milk. α-Lactalbumin represents about 25% of the whey proteins in bovine milk, whereas it represents over 40% of human milk. Thus there are two markets in the infant formula industry, one to deplete β-lactoglobulin and the other to supplement α-lactalbumin.

α-Lactalbumin is an important food ingredient and useful as an emulsifier and foaming agent, e.g., for salad dressing, cake mix, and the like, and is heat stable. β-Lactoglobulin is useful as a gelling agent in hams, surimi, and other foods, especially for use in Japan.

Several processes have been proposed for future commercial scale production of α-lactalbumin or β-lactoglobulin. All but one of these processes fall into three main categories: selective precipitation induced by adjustment of the solution properties, membrane separation based on differences in size, and selective adsorption. Precipitation and membrane separation processes are volume-dependent methods wherein the equipment capacity and manufacturing cost is proportional to the volume of solution processed and not the mass of product produced. For dilute protein solutions such as whey, large volumes of liquid must be processed to recover a fixed mass of protein. Adsorption processes are less volume dependent as capacity is tied more to the mass of product recovered and less to the volume of liquid processed. Nevertheless, all but one of the other proposed processes produce only purified α-lactalbumin or β-lactoglobulin, not both simultaneously. In other words, a single purified protein product is produced in conjunction with the production of an impure treated whey solution which is depleted in that protein and is typically contaminated with fat, lactose and minerals. The total revenues generated from producing a single purified protein product and an impure whey solution would likely be less than those generated by producing multiple pure protein products from the same stream of whey.

U.S. Pat. No. 5,420,249 to de Wit et al. relates to a selective precipitation process in which whey is contacted with a calcium-binding ion exchange resin to initiate the destabilization of α-lactalbumin. Next, the resin is separated from the treated whey. The treated whey is adjusted in pH and temperature to precipitate α-lactalbumin. The β-lactoglobulin remains in the treated whey. However, the de Wit process uses an ion exchanger to bind and remove calcium, not whey protein. Subsequent steps relate to the treatment of the product from the first step, the supernatant solution, which does not contain the ion exchanger.

U.S. Pat. No. 5,455,331 to Pearce applies to a selective precipitation process and does not involve an ion exchanger. The precipitate is enriched in α-lactalbumin, whereas the supernatant is enriched in β-lactoglobulin. This heat precipitation process has also been reported by Outinen et al. (1996) to produce a low density precipitate that is time-consuming and difficult to recover, and a precipitate that is contaminated with most of the other whey proteins except β-lactoglobulin.

U.S. Pat. No. 5,008,376 to Bottomley and U.S. Pat. No. 5,503,864 to Uchida et al. describe membrane-based processes wherein the separation is based on differences in size between the whey proteins. Neither process involves an ion exchanger and both processes involve membranes.

U.S. Pat. No. 4,918,008 to Gauri describes a process for producing whey protein hydrolysates suitable for pharmaceutical purposes. However, the process does not use ion exchangers.

Wang and Swaisgood (1993) describe a method for the production of β-lactoglobulin from whey using immobilized retinal. This method relies on the affinity binding site of β-lactoglobulin for retinal. However, the process does not suggest the production of α-lactalbumin, and it requires an expensive custom-made affinity adsorbent.

Haezebrouck et al. (1992) and Noppe et al. (1996) disclose a method to produce α-lactalbumin from whey using hydrophobic interaction chromatography. Removal of calcium from α-lactalbumin induces a conformational change in the protein, exposing a hydrophobic patch which binds to the hydrophobic adsorbent. Addition of calcium refolds the protein, buries the hydrophobic patch, causing elution of the bound alpha-lactalbumin. However, this method does not suggest the production of β-lactoglobulin, and the method requires an expensive adsorbent (phenyl-sepharose).

U.S. Pat. No. 5,756,680 to Ahmen et al. describes a process comprising adsorbing the proteins in whey to a cation exchange resin and sequentially eluting protein fractions using buffers at various pH and salt concentration. However, because the Ahmed et al. process uses salt for elution rather than changes in pH alone, several resin equilibration steps are needed to wash out the salt from the previous step before elution of the next protein in the sequence, which uses a lower salt concentration. These extra steps take additional time, reducing the productivity of the process. In addition, buffer costs are a major operating expense for large scale ion-exchange systems. Furthermore, use of salt for elution is undesirable because it is expensive to reprocess or use just once, and discharging it directly to the environment is a threat to plant and animal life. Another disadvantage of using salt for elution is that it is not very selective in eluting whey proteins which results in contamination of the eluted β-lactoglobulin with immunoglobulin using the Ahmed et al. process. For these reasons, it would be desirable to develop a process of the fractionation of α-lactalbumin and β-lactoglobulin from whey that does not require the use of salt. However, because the isoelectric points (the pH at which the net charge of the protein is zero) for α-lactalbumin and β-lactoglobulin are so close, 4.2–4.5 and 5.1, respectively, as reported by Eigel et al. (1984), use of pH only for uncontaminated fractionation on elution is not a method obvious to contemplate.

None of the above mentioned patents or references disclose processes whereby the proteins are bound to an ion exchanger and the bound proteins are eluted using different pH values alone, thus avoiding the increased cost, loss in productivity, and loss in purity associated with using salt for elution.

SUMMARY OF THE INVENTION

The present invention is directed to a process to yield a stream enriched in β-lactoglobulin and a second stream enriched in α-lactalbumin. Specifically the present invention is directed to a process for isolating α-lactalbumin and β-lactoglobulin from a solution containing whey proteins comprising fractionating the solution by contacting the solution with a cation exchanger to yield a bound β-lactoglobulin protein fraction and a bound α-lactalbumin protein fraction; and selectively eluting the bound β-lactoglobulin protein fraction and the bound α-lactalbumin protein fraction by changes in the eluting pH.

More specifically, the present invention is directed to a process for isolating β-lactoglobulin and α-lactalbumin which comprises adjusting a solution containing whey proteins to a pH of less than about 4.5; fractionating the adjusted solution by contacting the solution with a cation exchanger to yield a bound β-lactoglobulin fraction and a bound α-lactalbumin fraction; adjusting the bound fraction to a pH of about 4.9; eluting the β-lactoglobulin fraction to obtain substantially purified β-lactoglobulin; adjusting the bound fraction to a pH of about 6.5; and eluting the α-lactalbumin fraction to obtain substantially purified α-lactalbumin.

Advantageously, the present invention isolates and produces the two proteins, superior in terms of purity, from a solution containing whey proteins in a single contacting step, in one column without the use of salt for elution. The present invention is potentially very important to the large-scale cheese whey processing industry as it is economical to produce both whey proteins from a single batch of whey.

By fractionating multiple pure proteins from whey, the total revenues generated from the whey would likely be greater than those generated from producing a single purified protein product and an impure whey solution such as whey protein concentrate (WPC). Ultimately, whey processing may evolve in a direction analogous to crude oil processing, wherein, at the turn of the century, much of the crude oil was discarded as waste material to the environment, and only a fraction was refined into products. Today, nearly all crude oil is refined into value-added, useful products via a plurality of sophisticated separation processes and catalytic reactions that comprise large crude oil refineries. In the future the dairy industry may include whey "refineries" that process nearly all whey components into useful products, increasing the net value of whey.

For example, using the present invention, whey could be adjusted to a pH of about 3 and contacted with a cation exchanger to yield a bound fraction consisting of the whey proteins α-lactalbumin and β-lactoglobulin. Bound β-lactoglobulin could be eluted at a pH of about 4.9 and bound α-lactalbumin could be eluted at a pH of about 6.5. The remaining whey solution would be largely depleted of these proteins and could be fractionated by contacting it with an anion exchanger to yield a bound k-casein macropeptide (CMP) fraction. CMP would not bind to the cation exchanger because it does not carry a sufficient positive net charge at pH 3. The bound CMP fraction could be eluted using sodium chloride to produce another substantially pure whey protein from a single batch of whey.

The aims, objects, and advantages of the above-described multi-component value-added separation process will become apparent upon a complete reading of the Detailed Description, drawings, and attached claims below.

DETAILED DESCRIPTION OF INVENTION

Figure 1:
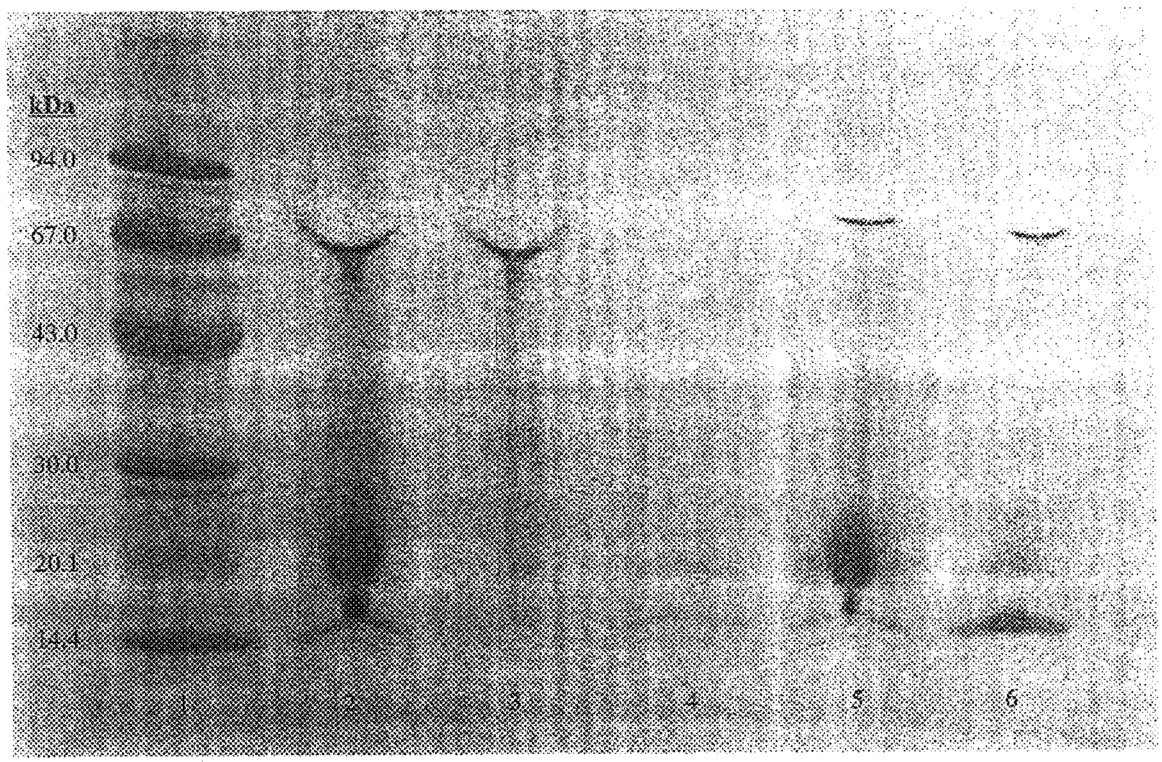
FIG. 1 is a gel electrophoresis printout showing the results in Example 1 from analyzing fractions by SDS-PAGE using Coomassie Blue R-350 staining of a PhastGel Gradient 10–15 polyacrylamide gel from Pharmacia.

The present invention is a means for the large-scale production of purified fractions of α-lactalbumin and β-lactoglobulin from a solution containing whey proteins by the selective elution of the bound proteins from a cation exchanger using increases in pH, while avoiding the use of salt for elution. The desired whey proteins are first bound to the ion exchange resin and contaminants are washed out. The process then proceeds by variation of ion exchange conditions to fractionate, concentrate and recover separately the two proteins from the column. The two whey proteins are eluted from the cation exchange column differentially by increasing the pH alone of the elution buffer. The elution buffer pH is raised to about 4.9 to elute β-lactoglobulin, then raised again to a pH of about 6.5 to elute α-lactalbumin.

The novelty of the present invention is based on the isoelectric point which is reported by Eigel et al. (1984), to be 4.2–4.5 for α-lactalbumin and 5.1 for βlactalbumin. As pH increases, one would expect α-lactalbumin to elute first, because its net charge switches from positive to negative at a lower pH than does β-lactoglobulin, which would elute second at a higher pH. However, this does not occur here. α-lactalbumin does not fully elute until about pH 6.5 which is 2.0 to 2.3 pH units above its isoelectric point, whereas the majority of the β-lactoglobulin elutes at about pH 4.6 as expected, because this pH is close to its isoelectric point.

The following describes in detail the production of α-lactalbumin and β-lactalbumin according to the present invention.

Whey Protein Solution

Any kind of solution containing whey proteins may be used. For example, whey may be used. Whey is defined as the thin, watery part of milk that separates from the thicker part (curds) after coagulation. The major dry-matter components in whey are lactose (approximately 75% on a total solids basis), protein (approximately 13%) and ash (approximately 9%). The ratio between the components changes depending on the process involved in its preparation. Examples of whey include cheese whey, rennet casein whey and products of these wheys such as whey protein concentrate, whey protein isolate, and dried whey. Reconstitution of dried whey products with water is necessary before use.

Clarifier

Small amounts of curds and lipids remain in these whey protein solutions, which are removed using a centrifuge, a cream separator or a clarifier prior to use, according to processes well known in the industry.

Adjust pH

The whey protein solution is then adjusted to about pH 4.5 or lower using an acid such as phosphoric acid, hydrochloric acid, sulfuric acid, acetic acid, lactic acid, or citric acid, according to methods known to the art.

Filter

Following pH adjustment, the whey may be filtered to avoid plugging of the ion exchanger if a fine microporous membrane or column packed with fine beads is utilized. Filtering is not necessary when using ion exchange membranes having large pores or columns packed with beads of large diameter. Filtering is accomplished by means known to art, such as, for example, 0.7 $\mu$m filter paper (Micro Filtration Systems, Dublin, Calif.). One advantage of filtering is that it allows increasing the flow rate of whey and other solutions through the ion exchanger without a significant increase in pressure drop or loss of performance.

Heat

Advantageously, the process can be conducted at elevated temperatures, ranging from 35° C. to 50° C., preferably at a temperature of about 40° C.

Cation Exchanger

In ion exchange chromatography, charged solute molecules (here the whey proteins) are reversibly adsorbed (bound) to immobilized ion exchange groups of opposite charge, while unbound substances can be washed out. Bound substances can then be eluted out by changing the buffer to make conditions unfavorable for binding of the solute molecules to the ion exchange matrix. The solute is thus released from the column. In cation exchange, positively charged solute molecules exchange with the positively charged mobile counter ions and bind with the negatively charged adsorbent. Ion exchange chromatography can be used to bind the desired material and wash contaminants out through the column, or, to bind contaminants and wash out the substances of interest.

The adjusted whey protein solution is contacted with a cation exchanger containing charged immobilized molecules such as carboxymethyl or sulfopropyl moieties to yield a first fraction consisting of adsorbed (bound) α-lactalbumin and β-lactoglobulin. The bound proteins are washed free of contaminating minerals, e.g. calcium, lactose and fat according to methods known to the art, such as a solution containing ethylenediaminetetraacetic acid tetrasodium salt (NaEDTA) to chelate divalent cations.

The binding of calcium ions to an affinity binding site on α-lactalbumin is speculated to play a role in the enhanced purity obtained by stripping away calcium using EDTA in the washing buffer and adding calcium to the pH 6.5 buffer. α-lactalbumin without calcium (apo-α-lactalbumin) is known to become more hydrophilic, and change in net charge when calcium binds to the high affinity binding site. Binding of calcium buries aromatic amino acids in α-lactalbumin, changing its structure and solution behavior.

A second fraction is collected by elution from the first fraction using a pH greater than about 4 but less than about 6.0, preferably a pH about 4.9, to yield a solution enriched in β-lactoglobulin.

A third fraction is collected by elution from the first fraction using a pH greater than that used in the first step, preferably a pH of about 6.5 or greater, to yield a solution enriched in α-lactalbumin. This step may also include the addition of a divalent cation, e.g. Ca, Mg, Zn, to the elution buffer to enhance desorption of α-lactalbumin.

The mechanism underlying this effect is not known. However, divalent cations bind to the affinity binding site of α-lactalbumin, inducing a conformation of change in the protein. This change possibly causes a change in net charge and hydrophobicity of α-lactalbumin that enhances its release from the cation exchanger. An alternative explanation may be that divalent cations such as Ca, Zn and Mg, which have an affinity for the cation exchanger, may displace bound α-lactalbumin. Both mechanisms may occur simultaneously.

Examples of materials used to form the cross-linked polymeric beads used for the cation exchanger include cellulose, agarose, or dextran, each containing charged immobilized moieties. Microporous polymeric membranes comprised of regenerated cellulose, polysulfone, or cellulose acetate and containing the charged immobilized moieties are also contemplated here. A further example includes microporous paper containing the charged immobilized moieties.

Methods of contacting cation exchangers with whey are well known in the art. Conventional methods of contact are described in the following references which are incorporated herein by reference for their description of contacting methods (Ayers et al., 1986; Etzel, 1995; Adisaputro et al., 1996).

Without wishing to be bound to any one theory one would have expected β-lactoglobulin to elute at the higher pH because its isoelectric point is higher.

EXAMPLES

In order to more fully illustrate the present invention, the following Examples are provided. The Examples, which make reference to the attached figures, are for illustration purposes only to aid in a more complete understanding of the invention. The Examples do not limit the scope invention disclosed and claimed herein in any fashion.

Example 1

A water-jacketed chromatography column (XK50/20, Pharmacia, Piscataway, N.J.) operated at 35° C. was packed with 100 ml of a sulphopropyl cation exchanger (SP HB2 GibcoCel beaded cellulose, Life Technologies, Rockville, Md.). Mozzarella cheese whey was adjusted to pH 3.0 using 1 M phosphoric acid and 500 ml was pumped into the column in upflow at a flow rate of 8 ml/min. The ion exchanger was washed with 180 ml of water to remove contaminants minerals, lactose and fat. The ion exchanger was washed with 385 ml of a solution of 0.2 M sodium citrate, 0.02 M ethylenediaminetetraacetic acid (EDTA) tetra sodium salt, pH 3. β-Lactoglobulin was eluted from the ion exchanger using 1280 ml of 0.2 M sodium citrate, pH 4.9.

α-Lactalbumin was eluted from the ion exchanger using 930 ml of 0.2 M sodium citrate, 0.05 M calcium chloride, pH 6.5.

Referring to FIG. 1, fractions were analyzed by SDS-PAGE using Coomassie Blue R-350 staining of a PhastGel Gradient 10–15 polyacrylamide gel from Pharmacia. Most of the protein in the whey was adsorbed onto the ion exchanger because the effluent from the ion exchanger was greatly reduced in protein content (lane 3). Washing the ion exchanger with the pH 3 buffer did not remove a significant amount of the adsorbed protein (lane 4). Elution at pH 4.9 yielded a fraction (lane 5) enriched in β-lactoglobulin and depleted in α-lactalbumin, whereas elution at pH 6.5 yielded a fraction (lane 6) enriched in α-lactalbumin and depleted in β-lactoglobulin. Bands were identified via molecular weight markers (lane 1). β-lactoglobulin has a molecular weight of 18.3 Kda (Eigel et al., 1984). The bottom band in lane 1 is α-lactalbumin.

Figure 2:
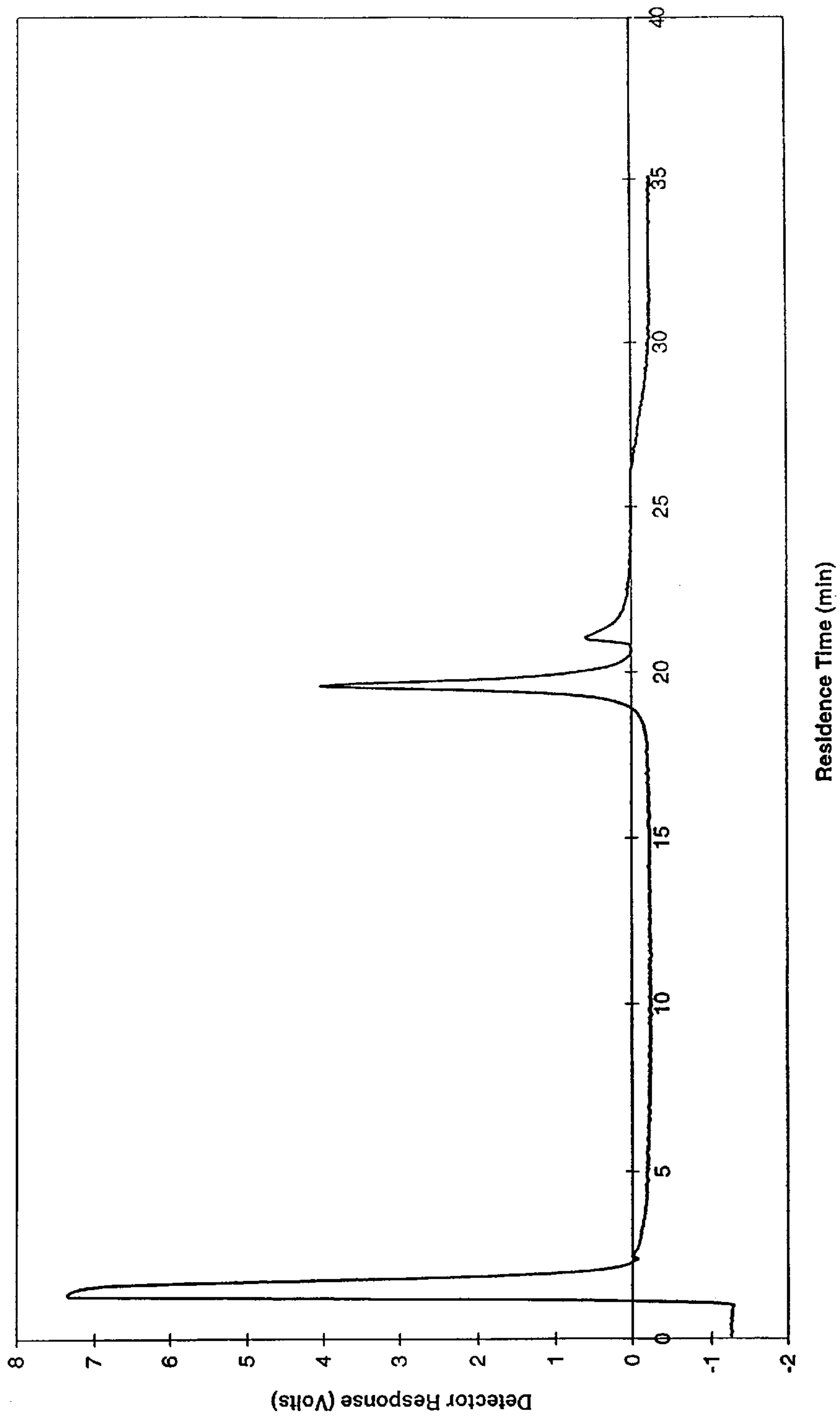
FIG. 2 is an HPLC chromatogram shown from fractions in Example 1 analyzed by HPLC.
Figure 3:
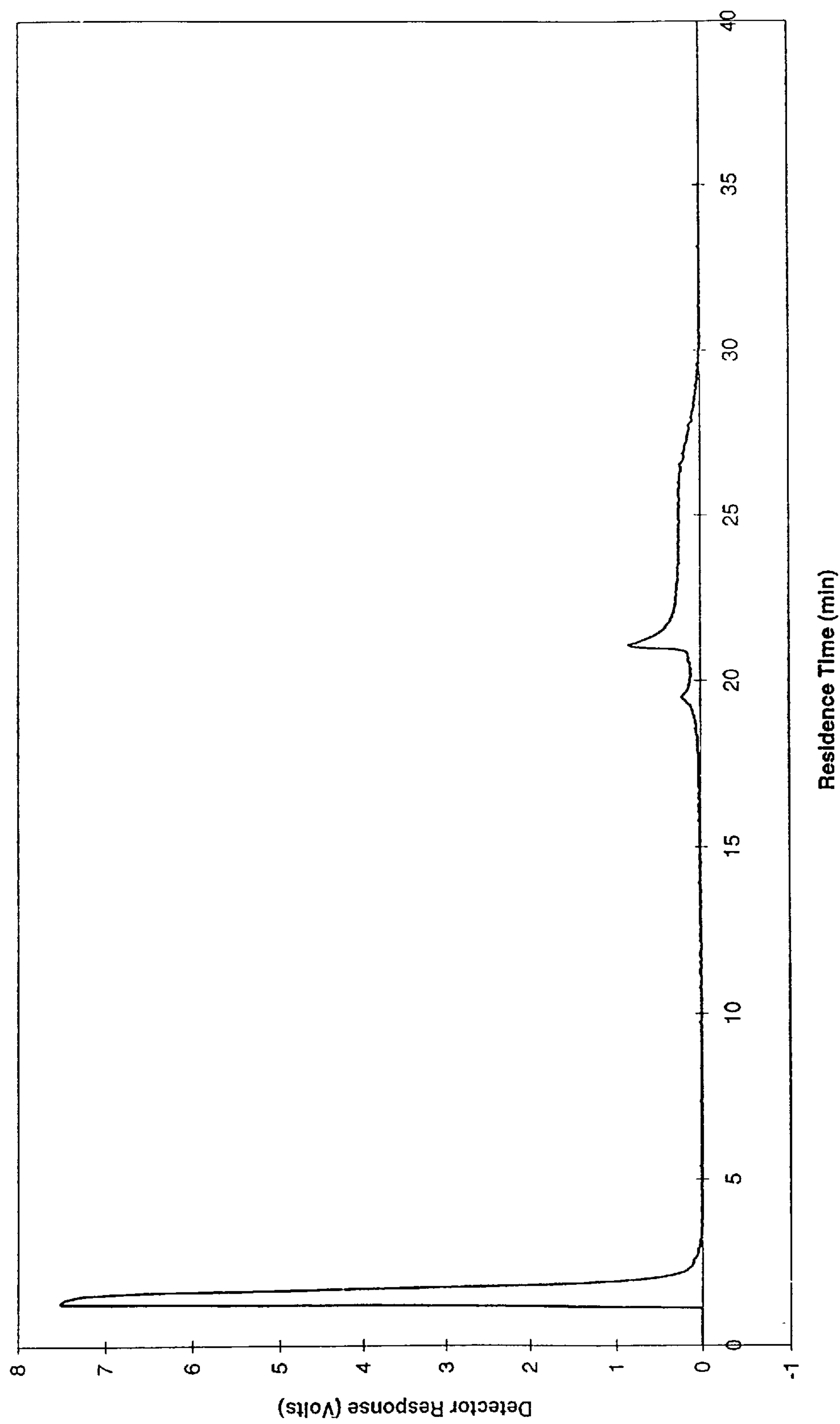
FIG. 3 is an HPLC chromatogram showing the pH 6.5 elution peak in Example 1 was enriched in alpha lactalbumin (RT=21.1 min).

Fractions were also analyzed by HPLC. A 100 μl sample was injected into Pharmacia Mono S HR 5/5 column using a gradient-programmed mobile phase starting with 0.05 M potassium phosphate pH 2 and ending with 0.05 M potassium phosphate, 1.5 M sodium chloride, pH 7. The flow rate was 1 ml/min and detection was at 214 nm. Peaks were identified by retention time (RT) using protein standards from Sigma. The pH 4.9 elution peak (FIG. 2) was enriched in β-lactoglobulin (RT=19.6 min) and the pH 6.5 elution peak (FIG. 3) was enriched in α-lactalbumin (RT=21.1 min).

Example 2

A water-jacketed chromatography column (XK50/20, Pharmacia, Piscataway, N.J.) operated at 40° C. was packed with 300 ml of a sulfopropyl cation exchanger (GibcoCel SP HB3, Life Technologies, Rockville, Md.). Mozzarella cheese whey was adjusted to pH 3.0 using 1 M phosphoric acid and 2250 ml was pumped into the column in downflow at a flow rate of 45 ml/min. The ion exchanger was washed with 750 ml of water to remove contaminants lactose, minerals, and fat. The ion exchanger was washed with 2600 ml of a solution of 0.2 M sodium citrate, 0.02 M ethylenediaminetetraacetic acid tetrasodium salt, pH 3. β-Lactoglobulin was eluted from the ion exchanger using 2300 ml of 0.2 M sodium citrate, pH 4.9. α-Lactalbumin was eluted from the ion exchanger using 2100 ml of 0.2 M L-histidine, 0.05 M calcium chloride, pH 6.5. Residual bound whey proteins were eluted using 1000 ml of 0.2 M ammonium buffer, pH 9.0.

Figure 4:
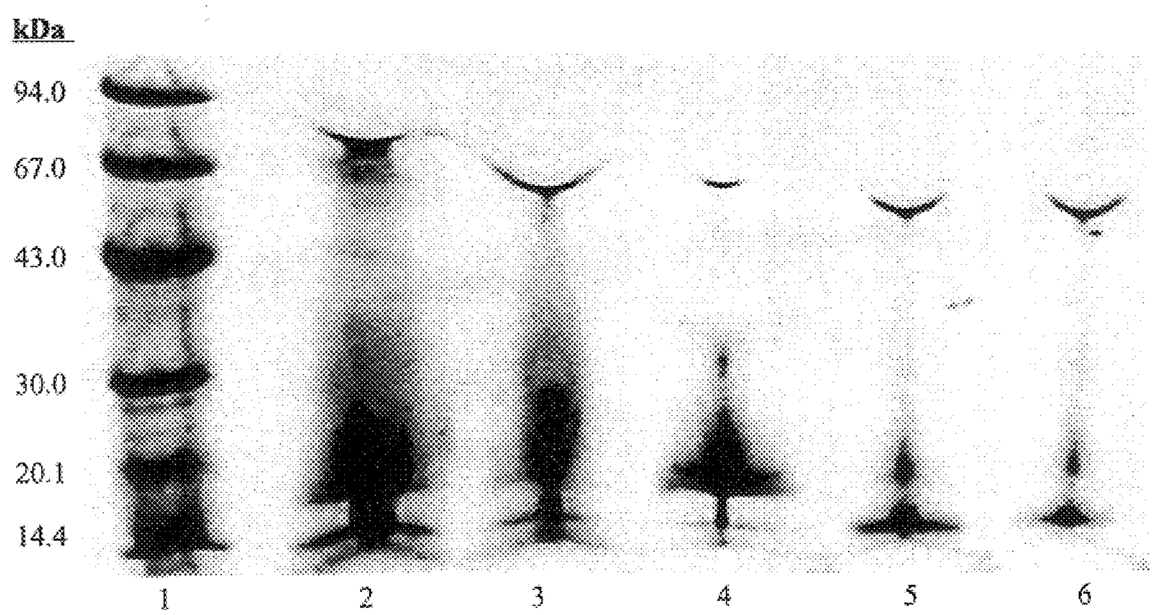
FIG. 4 is a gel electrophoresis printout showing the results in Example 2 from analyzing fractions by SDS-PAGE.

Fractions were analyzed by SDS-PAGE using Coomassie Blue R-350 staining of a PhastGel Gradient 10–15 polyacrylamide gel from Pharmacia (FIG. 4). Bands were identified via molecular weight markers (lane 1). Whey was applied to lane 2 with prior concentration. The effluent solution (whey and water) was concentrated five-fold by ultrafiltration (Centriprep-10, Millipore, Bedford, Mass.) and applied to lane 3. It contained the fraction of the whey proteins that did not bind to the cation exchanger. The pH 4.9 elution peak was concentrated two-fold and applied to lane 4. It was highly enriched in β-lactoglobulin and depleted in α-lactalbumin compared to whey. The pH 6.5 elution peak was concentrated two-fold and applied to lane 5. It was highly enriched in α-lactalbumin and depleted in β-lactoglobulin compared to whey. The pH 9.0 elution peak was concentrated five-fold and applied to lane 6. It contained a small amount of α-lactalbumin and β-lactoglobulin that was not removed in the previous elution steps, perhaps from tailing of the previous elution peaks.

Example 3

The experiment of Example 2 was repeated except for there were slightly different washing and elution volumes. Specifically, the ion exchanger was: washed with 650 ml of water; 1300 ml of 0.2 M sodium citrate, 0.02 M ethylenediaminetetraacetic acid tetrasodium salt, pH 3; β-lactoglobulin was eluted using 2300 ml of 0.2 M sodium citrate, pH 4.9; α-lactalbumin was eluted using 1900 ml of 0.2 M L-histidine, 0.05 M calcium chloride, pH 6.5; and residual bound whey proteins were eluted using 700 ml of 0.2 M ammonium buffer, pH 9.0.

Figure 5:
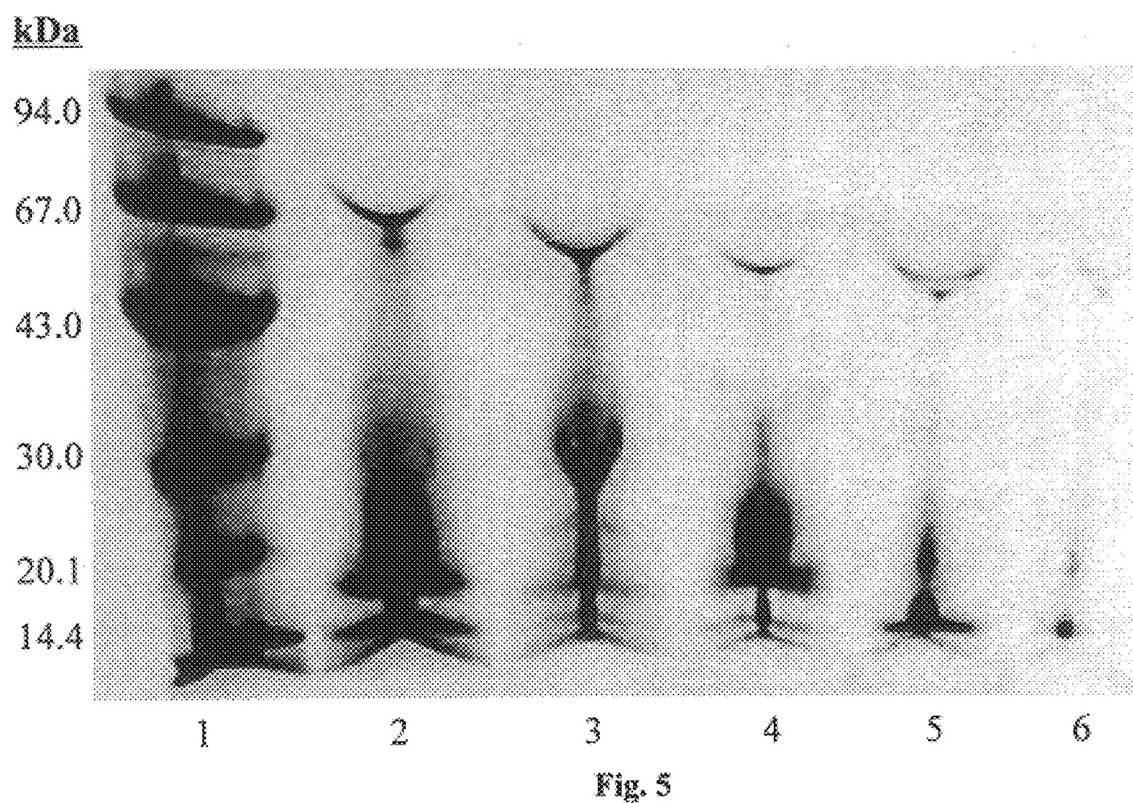
FIG. 5 is a gel electrophoresis printout showing the results in Example 3 from analyzing fractions by SDS-PAGE.

Fractions were analyzed by SDS-PAGE (FIG. 5) with the same samples run in each lane using the same sample preparation procedure as in Example 2. Bands were identified via molecular weight markers (lane 1). Whey was applied to lane 2. The effluent solution was concentrated five-fold and applied to lane 3. It contained the fraction of the whey proteins that did not bind to the cation exchanger and a large forked band at 30 kDa which is CMP. CMP does not bind to the cation exchanger because it is charged negative at pH 3.0. The pH 4.9 elution peak was concentrated two-fold and applied to lane 4. It was highly enriched in β-lactoglobulin and depleted in α-lactalbumin compared to whey. The pH 6.5 elution peak was concentrated two-fold and applied to lane 5. It was highly enriched in α-lactalbumin and depleted in β-lactoglobulin compared to whey. The pH 9.0 elution peak was concentrated five-fold and applied to lane 6. It contained a small amount of α-lactalbumin that was not removed in the previous elution steps, perhaps from tailing of the previous elution peak.

Example 4

The experiment of Example 2 was repeated except that magnesium chloride was substituted for calcium chloride in the elution of α-lactalbumin. Specifically, the ion exchanger was: washed with 550 ml of water; 1500 ml of 0.2 M sodium citrate, 0.02 M ethylenediaminetetraacetic acid tetrasodium salt, pH 3; β-lactoglobulin was eluted using 2600 ml of 0.2 M sodium citrate, pH 4.9; α-lactalbumin was eluted using 2400 ml of 0.2 M L-histidine, 0.05 M magnesium chloride, pH 6.5; and residual bound whey proteins were eluted using 1250 ml of 0.2 M ammonium buffer, pH 9.0.

Figure 6:
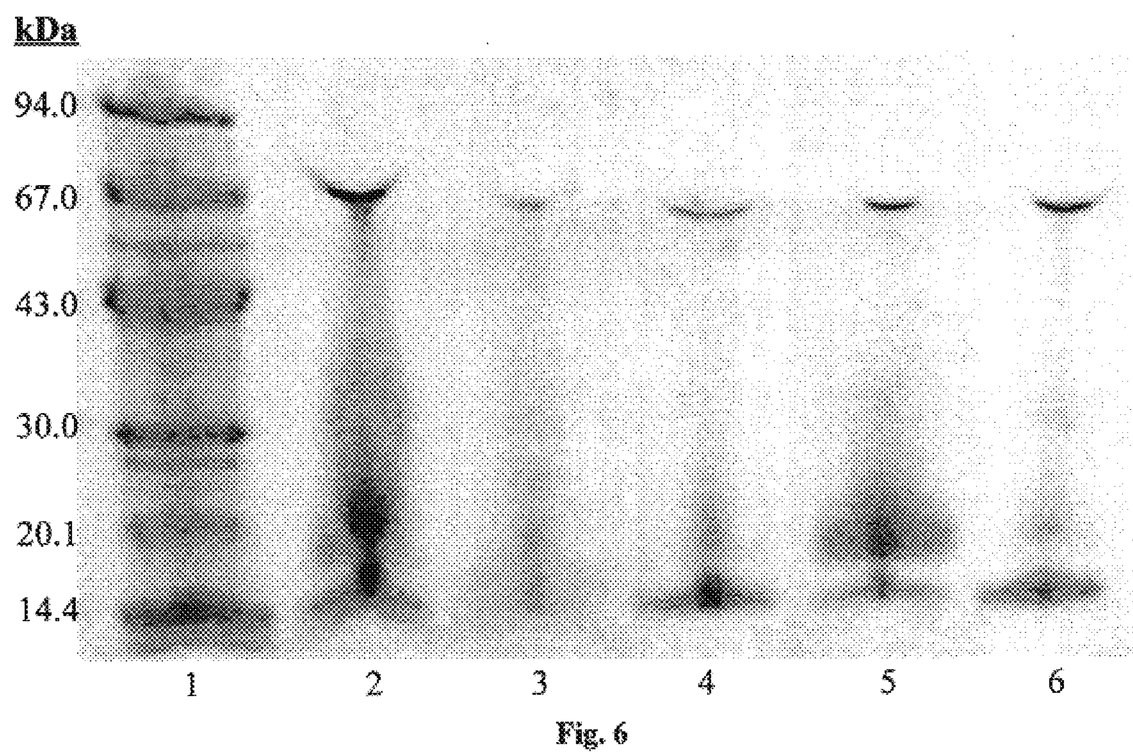
FIG. 6 is a gel electrophoresis printout showing the results in Example 4 from analyzing fractions by SDS-PAGE.

Fractions were analyzed by SDS-PAGE (FIG. 6) with the same sample preparation procedure as in Example 2. However, not all the samples were run in the same lanes. Bands were identified via molecular weight markers (lane 1), and whey was applied to lane 2. The effluent solution was concentrated five-fold and applied to lane 3. It contained the small fraction of the whey proteins that did not bind to the cation exchanger. The pH 4.9 elution peak was concentrated two-fold and applied to lane 5. It was highly enriched in β-lactoglobulin and depleted in α-lactalbumin compared to whey. The pH 6.5 elution peak was concentrated two-fold and applied to lane 4. It was highly enriched in α-lactalbumin and depleted in β-lactoglobulin compared to whey. The pH 9.0 elution peak was concentrated five-fold and applied to lane 6. It contained α-lactalbumin that was not removed in the previous elution steps. More residual α-lactalbumin was present in the pH 9.0 elution peak using magnesium chloride in the pH 6.5 elution peak compared to calcium chloride as in Example 2 and 3. Therefore, calcium chloride is preferred over magnesium chloride to enhance the desorption of α-lactalbumin. When calcium binds to the affinity binding site of α-lactalbumin, it changes the structure of the protein, burying a hydrophobic patch and making it more hydrophilic and changing its net charge. Magnesium also binds to the affinity site, but does not cause the same magnitude of structural and solution property changes. This mechanism is speculated to cause the lesser effect of magnesium chloride compared to calcium chloride in enhancing the desorption of α-lactalbumin from the cation exchanger.

Example 5

The experiment of Example 2 was repeated except that the wash step with of 0.2 M sodium citrate, 0.02 M ethylenediaminetetraacetic acid tetrasodium salt, pH 3 was omitted. Specifically, the ion exchanger was: washed with 650 ml of water; β-lactoglobulin was eluted using 2400 ml of 0.2 M sodium citrate, pH 4.9; α-lactalbumin was eluted using 1900 ml of 0.2 M L-histidine, 0.05 M calcium chloride, pH 6.5; and residual bound whey proteins were eluted using 600 ml of 0.2 M ammonium buffer, pH 9.0.

Figure 7:
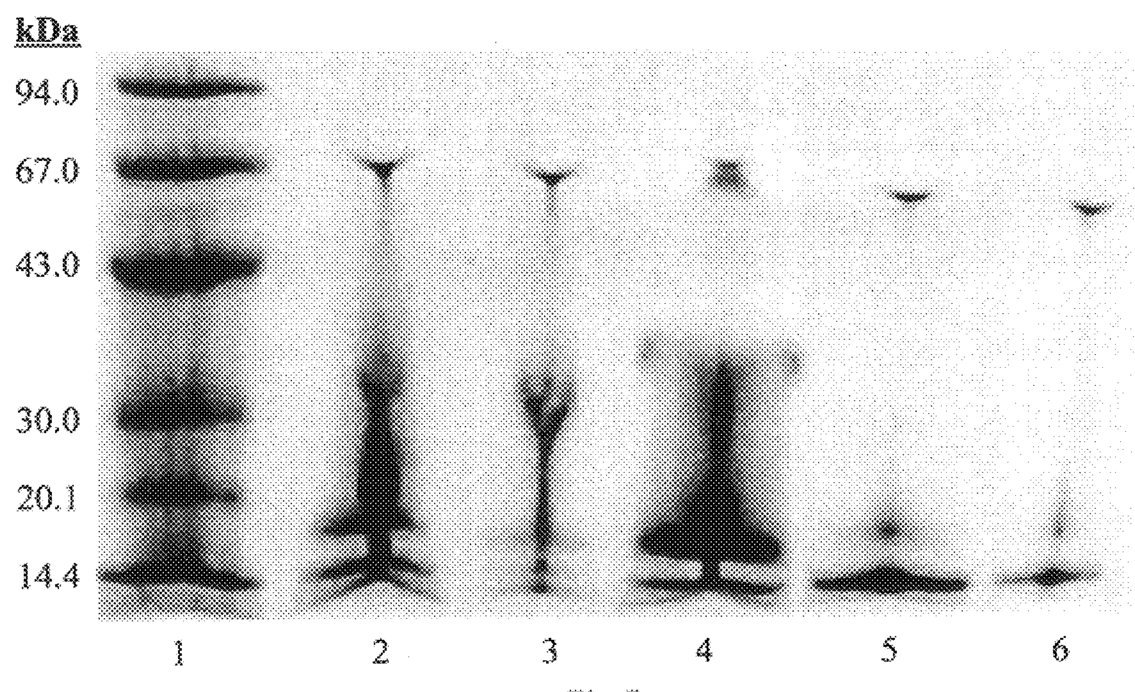
FIG. 7 is a gel electrophoresis printout showing the results in Example 5 from analyzing fractions by SDS-PAGE.

Fractions were analyzed by SDS-PAGE (FIG. 7) with the same sample preparation procedure as in Example 2. Bands were identified via molecular weight markers (lane 1), and whey was applied to lane 2. The effluent solution was concentrated five-fold and applied to lane 3. It contained the fraction of the whey proteins that did not bind to the cation exchanger column and a large forked band at 30 kDa which is CMP. The pH 4.9 elution peak was concentrated two-fold and applied to lane 4. It was highly enriched in β-lactoglobulin and depleted in α-lactalbumin compared to whey. However, it contained more α-lactalbumin compared to Examples 2 and 3 which included the wash step with of 0.2 M sodium citrate, 0.02 M ethylenediaminetetraacetic acid tetrasodium salt, pH 3. This observation is attributed to the incomplete chelation of calcium in this experiment compared to the experiments of Examples 2 and 3. Stripping calcium away from the bound α-lactalbumin is speculated to enhance its binding to the cation exchanger by converting it to apo-α-lactalbumin, which exposes a hydrophobic domain on the protein and changes its net charge. The pH 6.5 elution peak was concentrated two-fold and applied to lane 5. It was highly enriched in α-lactalbumin and depleted in β-lactoglobulin compared to whey. The pH 9.0 elution peak was concentrated five-fold and applied to lane 6. It contained a small amount of α-lactalbumin that was not removed in the previous elution steps.

Example 6

The experiment of Example 2 was repeated except that the pH 6.5 elution step was replaced with elution using 0.2 M sodium citrate, 0.05 M calcium chloride, pH 7.0. Specifically, the ion exchanger was: washed with 650 ml of water; 1300 ml of 0.2 M sodium citrate, 0.02 M ethylenediaminetetraacetic acid tetrasodium salt, pH 3; β-lactoglobulin was eluted using 2200 ml of 0.2 M sodium citrate, pH 4.9; α-lactalbumin was eluted using 1800 ml of 0.2 M sodium citrate, 0.05 M calcium chloride, pH 7.0; and residual bound whey proteins were eluted using 700 ml of 0.2 M ammonium buffer, pH 9.0.

Figure 8:
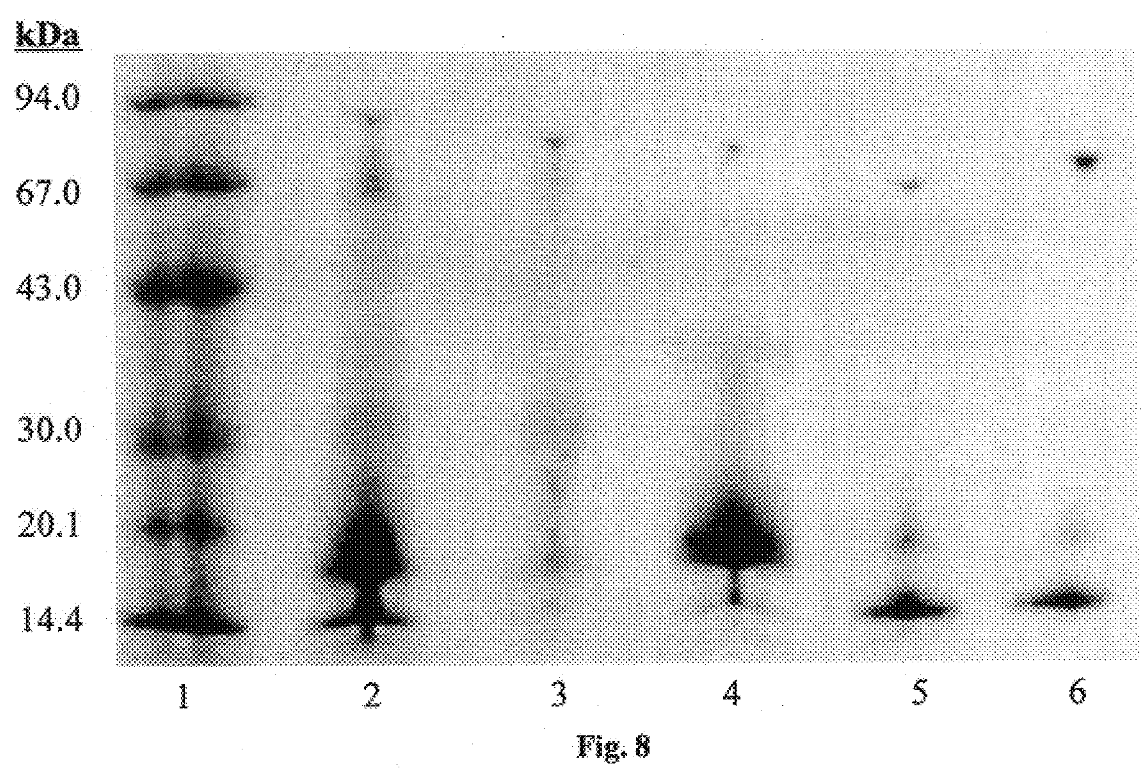
FIG. 8 is a gel electrophoresis printout showing the results in Example 6 from analyzing fractions by SDS-PAGE.

Fractions were analyzed by SDS-PAGE (FIG. 8) with the same sample preparation procedure as in Example 2. Bands were identified via molecular weight markers (lane 1), and whey was applied to lane 2. The effluent solution was concentrated five-fold and applied to lane 3. It contained the small fraction of the whey proteins that did not bind to the cation exchanger. The pH 4.9 elution peak was concentrated two-fold and applied to lane 4. It was highly enriched in β-lactoglobulin and depleted in α-lactalbumin compared to whey. The pH 7.0 elution peak was concentrated two-fold and applied to lane 5. It was highly enriched in α-lactalbumin and depleted in β-lactoglobulin compared to whey. The pH 9.0 elution peak was concentrated five-fold and applied to lane 6. It contained α-lactalbumin that was not removed in the previous elution steps. More residual α-lactalbumin was present in the pH 9.0 elution peak using sodium citrate, pH 7.0 with calcium for the elution of α-lactalbumin compared to histidine, pH 6.5 with calcium as in Examples 2 and 3. Citrate is a chelator for calcium, and may sequester the calcium, making it unavailable for binding to the affinity binding site on α-lactalbumin. When calcium binds to the affinity binding site of α-lactalbumin, it changes the structure of the protein, burying a hydrophobic patch, making it more hydrophilic, and changing its net charge. This mechanism is speculated to cause the lesser effect of citrate with calcium compared to histidine with calcium in enhancing the desorption of α-lactalbumin from the cation exchanger even though the citrate was used at a higher pH to compensate for the anticipated effect of chelation of calcium.

Example 7

The experiment of Example 2 was repeated except that the pH 6.5 elution step with histidine was replaced with elution using 0.2 M sodium phosphate, pH 7.5. Specifically, the ion exchanger was: washed with 650 ml of water; 1000 ml of 0.2 M sodium citrate, 0.02 M ethylenediaminetetraacetic acid tetrasodium salt, pH 3; βlactoglobulin was eluted using 2400 ml of 0.2 M sodium citrate, pH 4.9; α-lactalbumin was eluted using 1600 ml of 0.2 M sodium phosphate, pH 7.5; and residual bound whey proteins were eluted using 600 ml of 0.2 M ammonium buffer, pH 9.0.

Figure 9:
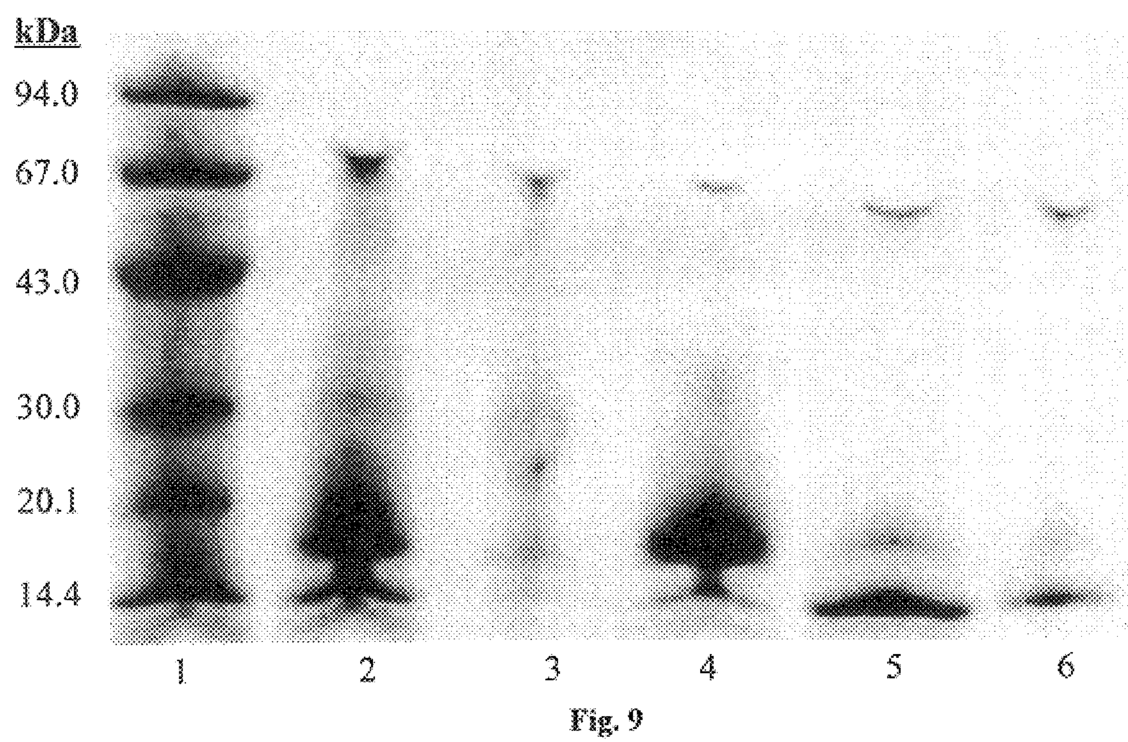
FIG. 9 is a gel electrophoresis printout showing the results in Example 7 from analyzing fractions by SDS-PAGE.

Fractions were analyzed by SDS-PAGE (FIG. 9) with the same sample preparation procedure as in Example 2. Bands were identified via molecular weight markers (lane 1), and whey was applied to lane 2. The effluent solution was concentrated five-fold and applied to lane 3. It contained the small fraction of the whey proteins that did not bind to the cation exchanger. The pH 4.9 elution peak was concentrated two-fold and applied to lane 4. It was highly enriched in β-lactoglobulin and depleted in α-lactalbumin compared to whey. The pH 7.5 elution peak was concentrated two-fold and applied to lane 5. It was highly enriched in α-lactalbumin and depleted in β-lactoglobulin compared to whey.

The pH 9.0 elution peak was concentrated five-fold and applied to lane 6. It contained α-lactalbumin that was not removed in the previous elution steps. Similar small amounts of residual α-lactalbumin were present in the pH 9.0 elution peak using sodium phosphate, pH 7.5 without calcium for elution of α-lactalbumin compared to histidine, pH 6.5 with calcium as in Examples 2 and 3. Calcium chloride could not be included in the phosphate solution because insoluble calcium phosphate formed, producing a cloudy white precipitate. Without calcium in the α-lactalbumin elution solution, a greater pH of 7.5 had to be used to elute fully the bound α-lactalbumin compared to Examples 2 and 3. When calcium binds to the affinity site of α-lactalbumin, it changes the structure of the protein, burying a hydrophobic patch, making it more hydrophilic, and changing its net charge. This mechanism is speculated to cause the lesser effect of phosphate without calcium compared to histidine with calcium in enhancing the desorption of α-lactalbumin from the cation exchanger. However, phosphate is less expensive than histidine. Nevertheless, the use of pH 7.5 with phosphate may have the undesirable effect of eluting some bound lactoferrin with the α-lactalbumin. Lactoferrin has an isoelectric point of 7.8 to 8.0, and is valuable as a pure protein by itself. The advantage of using histidine with calcium at pH 6.5 for elution of α-lactalbumin is that the lactoferrin would remain bound to the cation exchanger and could be recovered separately in pure form, increasing the revenues from the process.

It is understood that the invention is not confined to the particular construction and arrangement of parts herein illustrated and described, but embraces such modified forms thereof as come within the scope of the claims following the Bibliography.

BIBLIOGRAPHY

U.S. Pat. No. 5,008,376 to Bottomley

U.S. Pat. No. 5,420,249 to de Wit et al.

U.S. Pat. No. 4,918,008 to Gauri

U.S. Pat. No. 5,503,864 to Uchida et al.

U.S. Pat. No. 5,455,331 to Pearce

U.S. Pat. No. 5,756,680 to Ahmed et al.

Adisaputro, et al., 1996, *J. Liq. Chrom. & Rel. Technol.,* 19(9):1437–1450.

Ayers, et al., 1986*, New Zealand J. Dairy Sci. Technol.,* 21:21–35.

Eigel, et al., 1984, *J. Dairy Sci.,* 67:1599–1631.

Etzel, 1995, "Whey Protein Isolation and Fractionation Using Ion Exchangers," *Bioseparation Processes in Foods*, R. K. Singh and S. S. H. Rizvi (eds.), Marcel Dekker, New York, Ch. 12.

Haezebrouck et al., 1992*, Biochimica et Biophysica Acta,* 1122:305–310.

Noppe et al., 1996, *J. Chromat.* 719:327–331.

Outinen et al., 1996, *Levensm-Wiss. u.-Technol.,* 29:411–417.

Wang and Swaisgood, 1993, *J.Dairy Sci.,* 76:1895–1901.

What is claimed is:

1. A process for isolating β-lactoglobulin and α-lactalbumin which comprises the steps of:

a. adjusting a whey protein solution to a pH of less than about 4.5;

b. fractionating the adjusted solution by contacting the solution with a cation exchanger to yield a bound fraction containing β-lactoglobulin and α-lactalbumin;

c. adjusting the fraction bound to the cation exchanger in step b to a pH of about 4.0 to 6.0;

d. in the absence of sodium chloride, eluting at the pH of step c. a β-lactoglobulin fraction to obtain a substantially purified β-lactoglobulin fraction and a remaining fraction on the cation exchanger;

e. adjusting the remaining fraction bound to the cation exchanger from step d. to a pH of about 6.5 or greater; and f. in the absence of sodium chloride, eluting at the pH of step e. an α-lactalbumin fraction to obtain a substantially purified α-lactalbumin fraction.

2. The process of claim 1 wherein the cation exchanger comprises porous membranes containing charged immobilized moieties.

3. The process of claim 1 conducted at a temperature of between about 35° C. and 50° C.

4. The process of claim 1 conducted at a temperature of about 40° C.

5. The method of claim 1, wherein in step c. the fraction bound to the cation exchanger in step b. is adjusted to a pH of about 4.9.

6. The method of claim 1, wherein in step e. the remaining fraction bound to the cation exchanger from step d. is adjusted to a pH of about 6.5.

* * * * *